(12) United States Patent
Furuya et al.

(10) Patent No.: US 7,595,040 B2
(45) Date of Patent: Sep. 29, 2009

(54) DEAMIDATED INTERFERON-β

(75) Inventors: Kenji Furuya, Brisbane, CA (US); Deborah Johnson-Jackson, Canby, CA (US); Diana Tierra Ruscio, Martinez, CA (US)

(73) Assignee: Novartis Vaccines And Diagnostics, Inc., Emeryville, CA (US)

( * ) Notice: Subject to any disclaimer, the term of this patent is extended or adjusted under 35 U.S.C. 154(b) by 252 days.

(21) Appl. No.: 11/271,516

(22) Filed: Nov. 10, 2005

(65) Prior Publication Data

US 2006/0120998 A1 Jun. 8, 2006

Related U.S. Application Data

(60) Provisional application No. 60/626,837, filed on Nov. 10, 2004.

(51) Int. Cl.
*A61K 38/21* (2006.01)
*C07K 14/565* (2006.01)

(52) U.S. Cl. ..................... 424/85.6; 530/351

(58) Field of Classification Search ........................ None
See application file for complete search history.

(56) References Cited

U.S. PATENT DOCUMENTS

| 4,588,585 | A | 5/1986 | Mark et al. |
|---|---|---|---|
| 4,737,462 | A | 4/1988 | Mark et al. |
| 4,959,314 | A | 9/1990 | Mark et al. |
| 5,905,082 | A | 5/1999 | Roberts et al. |
| 6,696,423 | B1 | 2/2004 | Barsoum et al. |
| 2003/0113764 | A1 | 6/2003 | Bodary et al. |
| 2003/0119042 | A1 | 6/2003 | Rosado et al. |
| 2003/0190307 | A1 | 10/2003 | DiBiase et al. |
| 2003/0229042 | A1 | 12/2003 | Barsoum et al. |

FOREIGN PATENT DOCUMENTS

| EP | 0 948 358 B1 | 7/2004 |
|---|---|---|
| WO | WO 98/28007 | 7/1998 |
| WO | WO 2004/087753 A1 | 10/2004 |

OTHER PUBLICATIONS

Mikayama et al. Proc. Natl. Acad. Sci. USAvol. 90, pp. 10056-10060.*
Voet et al. Biochemistry John Wiley & Sons, Inc., pp. 126-128 and 228-234.*
Mark et al., "Modified Human Fibroblast Interferon," Application No. 435,154, filed Oct. 19, 1982.
Lathe et al., "DNA engineering: the use of enzymes, chemicals and and oligonucleotides to restructure DNA sequences in vitro," Genetic Engineering Academic Press, 1983, pp. 1-56.
Taniguchi et al, "The nucleotide sequences of human fibroblast interferon cDNA," Gene, 10 (1980) 11-15.
Derynck et al., "Isolation and structure of a human fibroblast interferon gene," Nature, vol. 285, Jun. 19, 1989, pp. 542-547.
Smith et al., "Constructed Mutants Using Synthetic Oligodeoxyribonucleotides as Site-Specific Mutagens," Genetic Engineering, Pinciples and Methods, vol. 3 (1981) pp. 1-32.
International Search Report dated Jul. 10, 2006 from related International Application No. PCT/US2005/040758.
Kawasaki, Hiroaki et al., "A protein with antimicrobial activity in the skin of Schlegel's green tea frog *Rhacophorus schlegelii* (Rhacophoridae) identified as histone H2B." Biochemical and Biophysical Research Communications. Dec. 26, 2003, vol. 312, No. 4, Dec. 26, 2003, pp. 1082-1086, XP002386626 ISSN: 0006-291X.

* cited by examiner

*Primary Examiner*—Prema Mertz
(74) *Attorney, Agent, or Firm*—Cozette M McAvoy

(57) ABSTRACT

Interferon-β protein analogs in which the asparagine at position 25, numbered in accordance with native interferon-β, is deamidated exhibit a biological activity of native human interferon-β at an increased level and do not require HA for protein stabilization. The deamidated product is suitable for large scale manufacturing for incorporation in HA-containing or HA-free therapeutics for treatment of diseases including multiple sclerosis. An endoproteinase-C peptide map technique that produces a fingerprint profile for proteins using an enzymatic digest followed by RP-HPLC is also useful in quality control as an ID and/or quantitative test for the deamidated products.

11 Claims, 14 Drawing Sheets

```
                  5              10              15              20
MetSerTyrAsnLeu LeuGlyPheLeuGln ArgSerSerAsnPhe GlnCysGlnLysLeu
                 25              30              35              40
LeuTrpGlnLeuAsn GlyArgLeuGluTyr CysLeuLysAspArg MetAsnPheAspIle
                 45              50              55              60
ProGluGluIleLys GlnLeuGlnGlnPhe GlnLysGluAspAla AlaLeuThrIleTyr
                 65              70              75              80
GluMetLeuGlnAsn IlePheAlaIlePhe ArgGlnAspSerSer SerThrGlyTrpAsn
                 85              90              95             100
GluThrIleValGlu AsnLeuLeuAlaAsn ValTyrHisGlnIle AsnHisLeuLysThr
                105             110             115             120
ValLeuGluGluLys LeuGluLysGluAsp PheThrArgGlyLys LeuMetSerSerLeu
                125             130             135             140
HisLeuLysArgTyr TyrGlyArgIleLeu HisTyrLeuLysAla LysGluTyrSerHis
                145             150             155             160
CysAlaTrpThrIle ValArgValGluIle LeuAgAsnPheTyr PheIleAsnArgLeu
                165             170             175             180
ThrGlyTyrLeuArg Asn---
```

FIG. 1

DEAMIDATED INTERFERON-β

CROSS-REFERENCE TO RELATED APPLICATIONS

This application claims priority to U.S. Provisional Patent Application No. 60/626,837, filed Nov. 10, 2004, titled DEAMIDATED INTERFERON-BETA, the disclosure of which is incorporated herein by reference in its entirety and for all purposes.

BACKGROUND

1. Technical Field

This invention is in the general area of biologically active protein chemistry. More specifically it relates to mutationally and chemically altered Interferon-β analogs that differ from the native protein by substitutions, deletions or modifications of cysteine, asparagine and other residues.

2. Background Art

Interferon-β has been found to be useful in the treatment of human disease, in particular multiple sclerosis. Multiple sclerosis (MS) is a chronic, often disabling disease of the central nervous system that occurs when a protective sheath surrounding nerve fibers breaks down. About thirty percent of MS patients suffer from a relapsing-remitting form of the disease in which symptoms disappear totally or partially after a flare-up and are followed by a period of stability that can last for months or years. Administration of beta interferon (Interferon-β or IFN-β has been demonstrated to reduce the frequency of MS flare-ups. As a result, Interferon-β based pharmaceuticals have become a valuable tool in management and treatment of MS.

Recombinant DNA (rDNA) techniques have been developed to facilitate the large scale manufacturing of Interferon-β based pharmaceuticals. One problem in particular that needed to be addressed by these techniques was that human beta interferon, the amino acid sequence of which is provided in FIG. 1 (SEQ ID NO: 1), contains cysteine residues at positions 17, 31, and 141, Gene (1980) 10:11-15 and Nature (1980) 285:542-547), at least some of which are non-essential to their activity but are free to form undesirable intermolecular or intramolecular links. In the course of the microbial preparation of IFN-β by rDNA techniques, it has been observed that dimers and oligomers of IFN-β are formed in extracts containing high concentrations of IFN-β due to this intermolecular linking. This multimer formation renders purification and isolation of IFN-β very laborious and time-consuming and necessitates several additional steps in purification and isolation procedures such as reducing the protein during purification and reoxidizing it to restore it to its original conformation, thereby increasing the possibility of incorrect disulfide bond formation. In addition, this multimer formation has been associated with low specific biological activity.

In order to address these issues, refined rDNA techniques have been developed to alter microbially produced biologically active IFN-β protein analogs in a manner that does not affect their activity adversely, but reduces or eliminates their ability to form intermolecular crosslinks or intramolecular bonds that cause the protein to adopt an undesirable tertiary structure (e.g., a conformation that reduces the activity of the protein). Directed mutagenesis techniques have been successfully used to form mutationally altered biologically active protein analogs (a "protein analog" refers herein to a synthetic protein in which one or more amino acids has been genetically and/or chemically modified and that retains a biological activity of the parent protein) that retain a desired activity of their parent proteins but lack the ability to form intermolecular links or undesirable intramolecular disulfide bonds. Synthetic protein analogs of IFN-β biologically active protein which have the cysteine residue at position 17 deleted or replaced by another amino acid have been found to have the desired activity and characteristics.

In particular, Interferon-β 1b (IFN-β1b), a synthetic, recombinant protein analog of IFN-β, is a biologically active protein which has the cysteine residue at position 17 replaced by a serine residue has been made. As a microbially produced protein, IFN-β1b is unglycosylated. It also has an N-terminal methionine deletion. IFN-β 1b has been formulated into a successful pharmaceutical marketed as Betaseron® that has been shown to be effective for treatment and management of MS. This protein analog, materials and techniques for its manufacture, its formulation as a therapeutic and its use to treat MS are described and claimed in a number of US Patents and applications including application Ser. No. 435,154, filed Oct. 19, 1982; U.S. Pat. No. 4,588,585, issued May 13, 1986; U.S. Pat. No. 4,737,462, issued Apr. 12, 1988; and U.S. Pat. No. 4,959,314, issued Sep. 25, 1990; each of which is incorporated by reference herein for their disclosure of these features.

Large scale manufacturing of IFN-β for pharmaceuticals is also conducted from mammalian sources, in particular Chinese hamster ovary (CHO) cells. This IFN-β analog, referred to as IFN-β 1a, lacks the Ser17 mutation of IFN-β 1b and is glycolsylated. IFN-β 1a is formulated into therapeutic products marketed as Avonex® and Rebith®.

As with most therapeutics, there is a continual desire to identify and manufacture more potent biologically active agents. It the case of IFN-β based pharmaceuticals, a IFN-β analog with increased biological activity would be desirable.

In addition, some IFN-β pharmaceutical formulations, including Betaseron®, contain human albumin (HA or HSA), a common protein stabilizer. HA is a human blood product and is in increasingly low supply. Accordingly, more recently there has been a desire for HA-free drug formulations, and a stable and effective HA-free IFN-β formulation would be desirable.

SUMMARY OF THE INVENTION

The present invention addresses these needs by providing deamidated Interferon-β. The deamidated IFN-β is a human interferon-β protein analog in which the asparagine at position 25, numbered in accordance with native interferon-β, is deamidated. The deamidated product exhibits a biological activity of native human interferon-β at an increased level and does not require HA for protein stabilization.

In a specific embodiment, the deamidated IFN-β is a synthetic human interferon-β 1b protein analog in which cysteine at position 17, numbered in accordance with native interferon-β, is deleted or replaced by a neutral amino acid, in particular serine, and the asparagine at position 25, is deamidated such that it becomes a cyclic imide, aspartate or isoaspartate residue. The deamidated product exhibits the desired biological activity of native human interferon-β (e.g., cellular cytopathic effects or antiproliferative activity, such as have been shown to be correlated with reducing the frequency of multiple sclerosis flare-ups) at an increased level relative to its IFN-β parent protein. In addition, the enhanced biological activity is observed in an HA-free formulation of the protein analog.

Formulations of the active protein analog compounds in therapeutic compositions and methods of making and use are also provided.

In addition, an endoproteinase-C peptide map technique that produces a fingerprint profile for proteins using an enzymatic digest of a reduced protein sample at relatively low pH, followed by chromatographic resolution of peptide fragments, useful in quality control as an ID test for the deamidated products is provided.

These and other objects and features of the invention will become more fully apparent when the following detailed description of the invention is read in conjunction with the accompanying drawings.

BRIEF DESCRIPTION OF THE DRAWINGS

FIG. 1 is a diagram of the amino acid sequence of IFN-β (SEQ ID NO: 1).

DESCRIPTION OF SPECIFIC EMBODIMENTS OF THE INVENTION

The compounds, compositions, materials and associated techniques and uses of the present invention will now be described with reference to several embodiments. Important properties and characteristics of the described embodiments are illustrated in the structures in the text. While the invention will be described in conjunction with these embodiments, it should be understood that the invention it is not intended to be limited to these embodiments. On the contrary, it is intended to cover alternatives, modifications, and equivalents as may be included within the spirit and scope of the invention as defined by the appended claims. In the following description, numerous specific details are set forth in order to provide a thorough understanding of the present invention. The present invention may be practiced without some or all of these specific details. In other instances, well known process operations have not been described in detail in order not to unnecessarily obscure the present invention.

Introduction

The present invention provides deamidated Interferon-β. The deamidated IFN-β is a human interferon-β protein analog in which the asparagine at position 25, numbered in accordance with native interferon-β, is deamidated. Asn deamidates to Asp or iso-Asp via a cyclic imide intermediate. The deamidated product exhibits a biological activity of native human interferon-β at an increased level and does not require HA for protein stabilization. Formulations of the active protein analog compounds in therapeutic compositions and methods of making and use are also provided.

A "protein analog" refers herein to a synthetic protein in which one or more amino acids has been genetically and/or chemically modified and that retains a biological activity of the parent protein, such as cellular cytopathic effects or antiproliferative activity. Such biological activity has been shown to be correlated with other specific biological activities, such as reducing the frequency of multiple sclerosis flare-ups.

In a specific embodiment, the deamidated IFN-β is a purified and isolated synthetic human interferon-β 1b protein analog in which cysteine at position 17, numbered in accordance with native interferon-β, is deleted or replaced by a neutral amino acid, in particular serine, and the asparagine at position 25, is deamidated. In specific embodiments, the Asn25 is deamidated to an aspartate, iso-aspartate or cyclic imide residue (e.g., IFN-$\beta_{ser17,asp25}$, IFN-$\beta_{ser17,iso-asp25}$ or IFN-$\beta_{ser17,cyclic-imide25}$, respectively). The deamidated product exhibits a biological activity of native human interferon-β at an increased level relative to IFN-β 1b. In addition, the enhanced biological activity is observed in an HA-free formulation of the protein analog, enabling an HA-free IFN-β 1b therapeutic.

Figure 2:
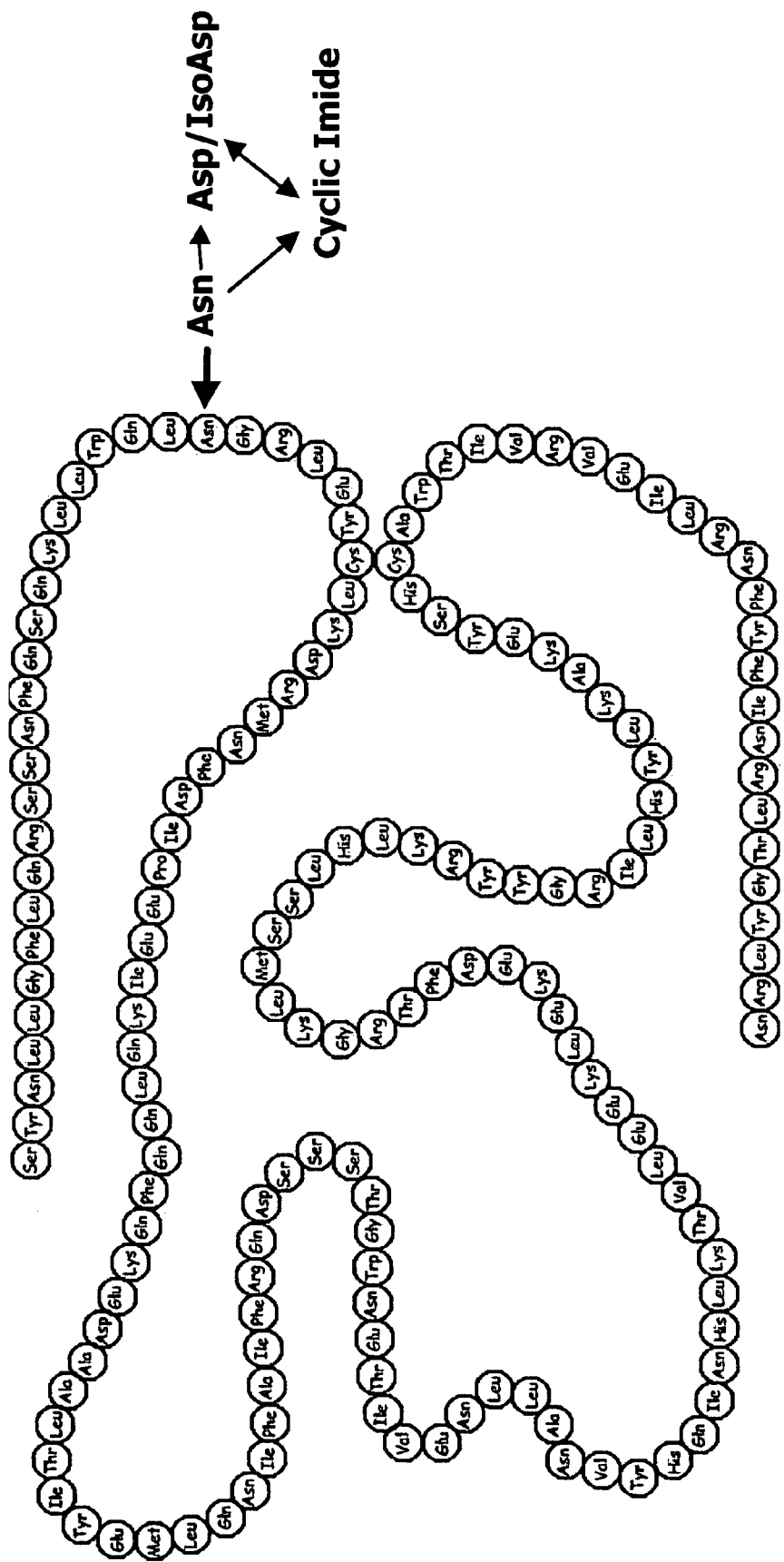
FIG. 2 is diagram of the amino acid sequence of IFN-β (SEQ ID NO: 2) 1b indicating the site and nature of the deamidation in accordance with the present invention.
Figure 3:
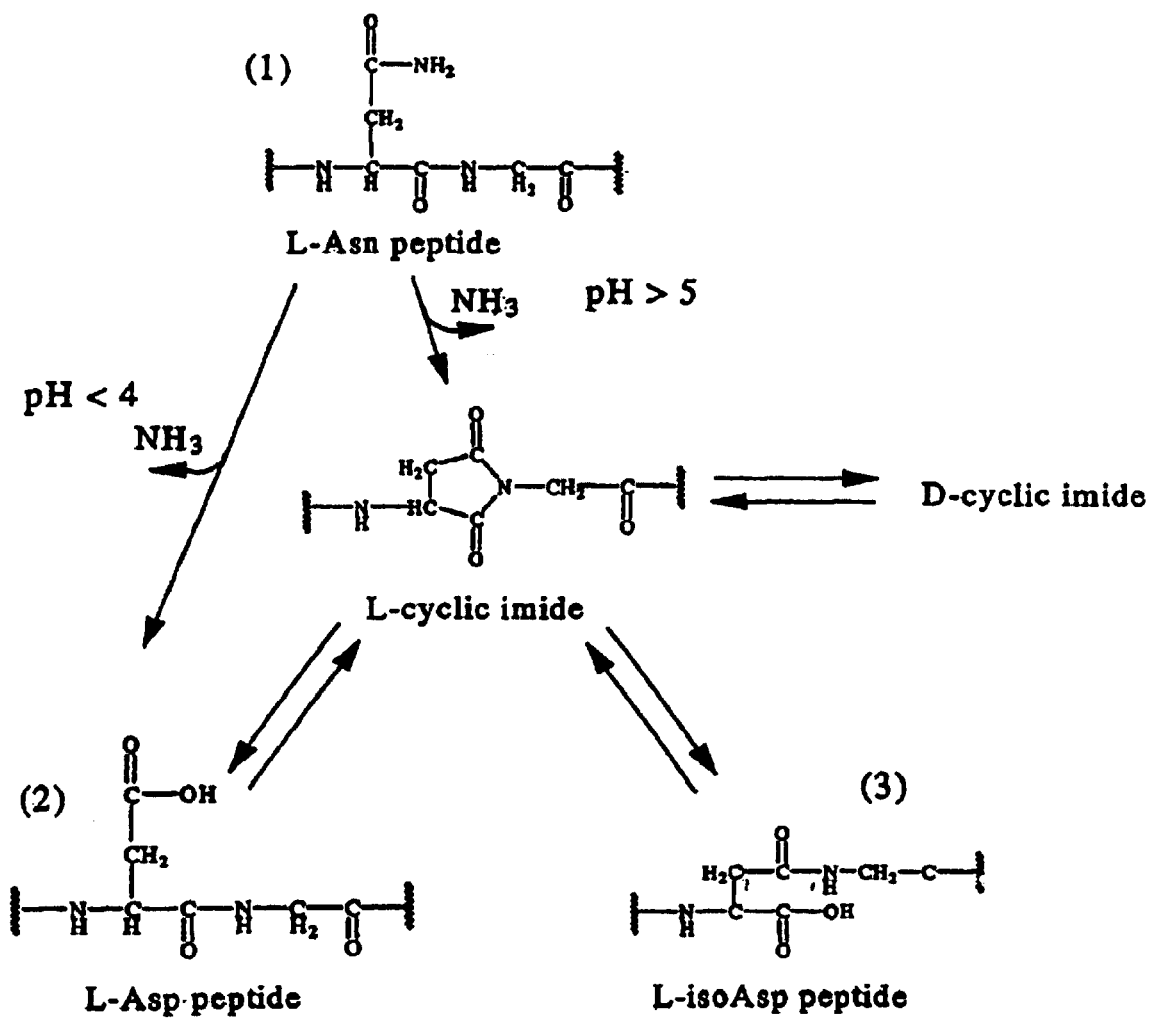
FIG. 3 is diagram illustrating the Asn deamidation pathway with reference to INF-β Asn25 deamidation in accordance with the present invention.
Figure 4:
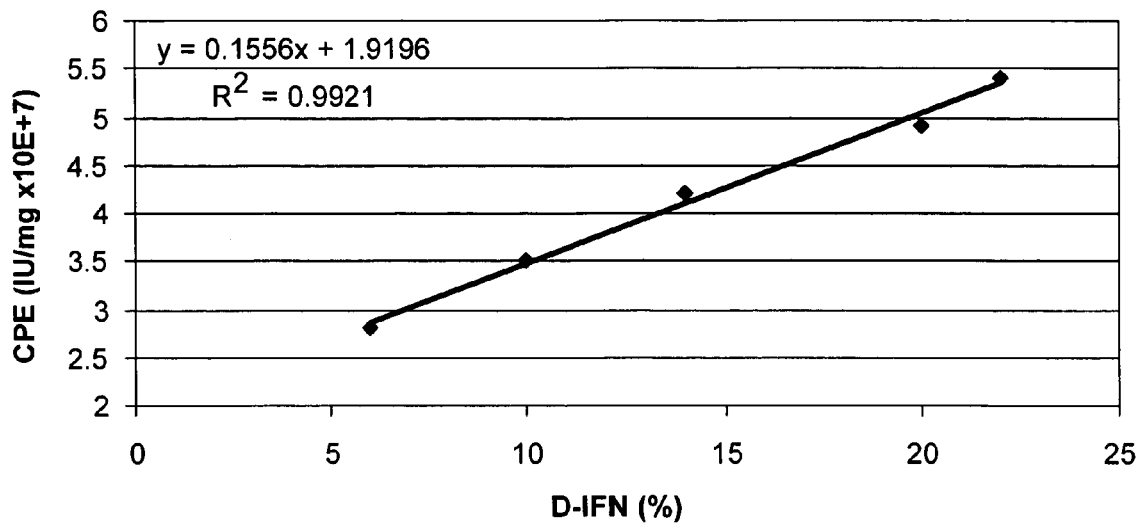
FIGS. 4-11 show plots of the potency versus the amount of deamidated IFN-β 1b in various HA-free IFN-β stability drug substance and product lots in accordance with one aspect of the invention.
Figure 5:
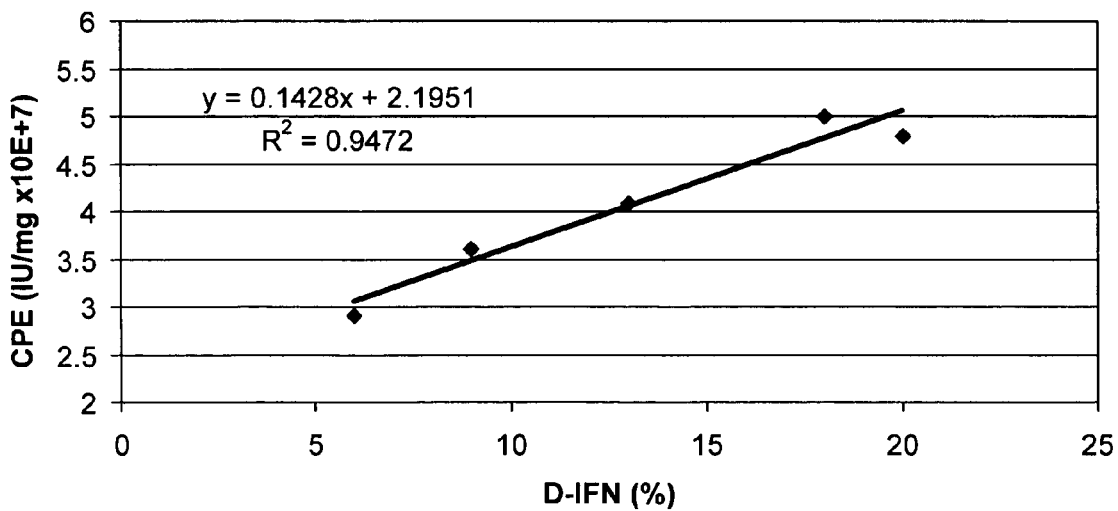
Figure 6:
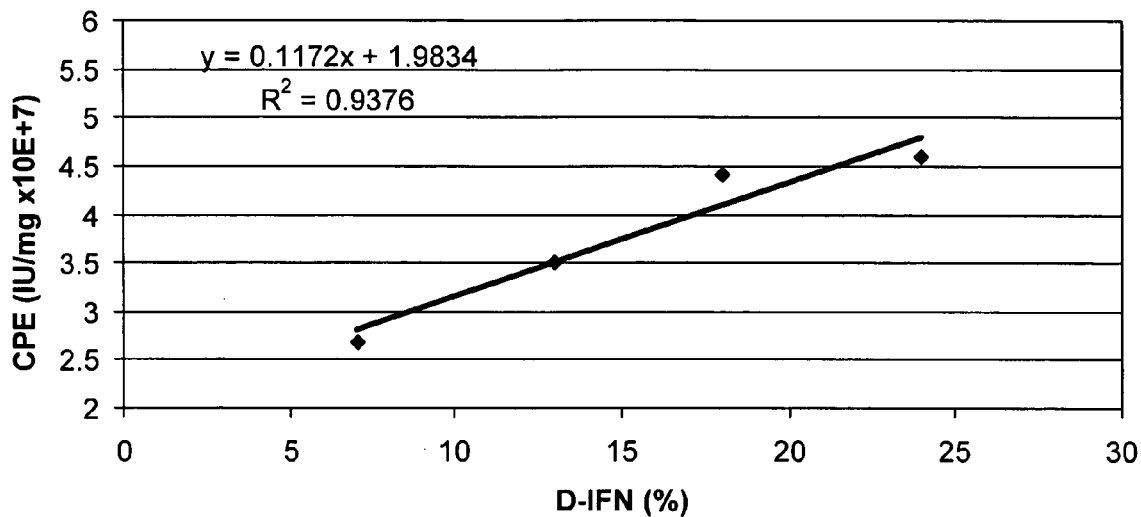
Figure 7:
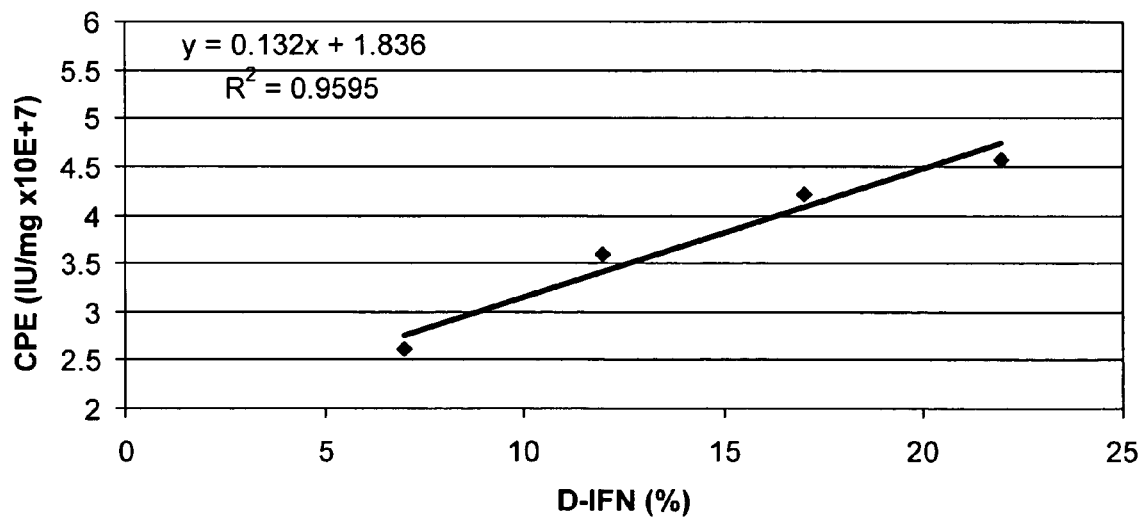
Figure 8:
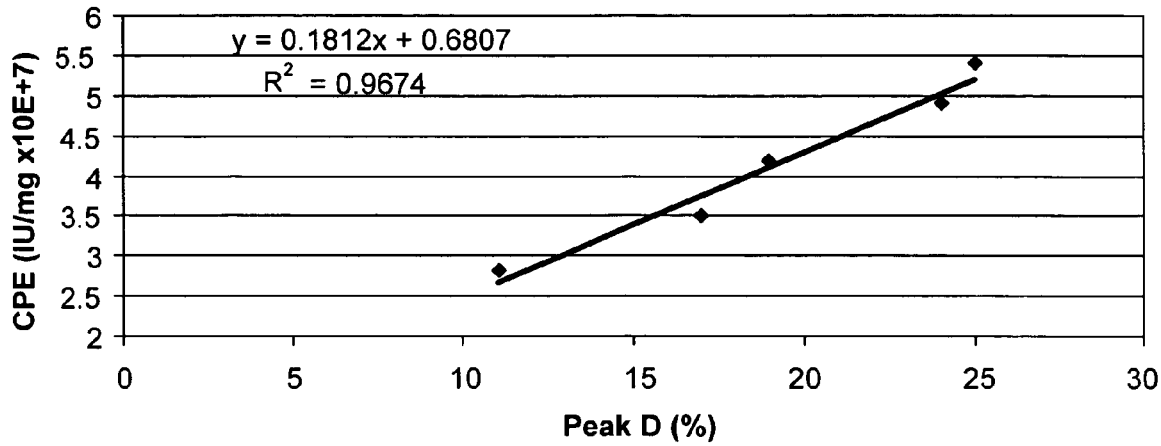
Figure 9:
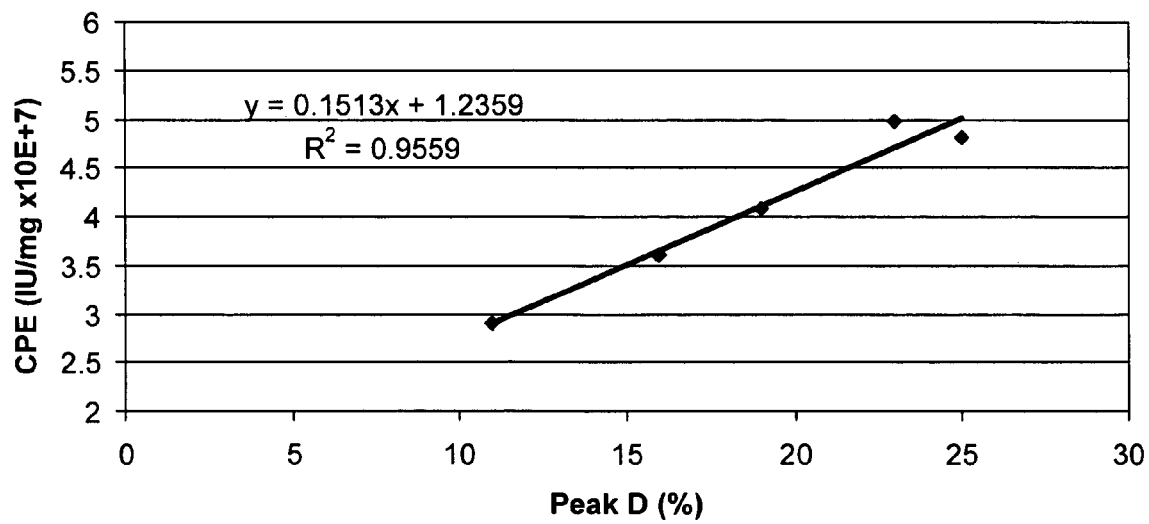
Figure 10:
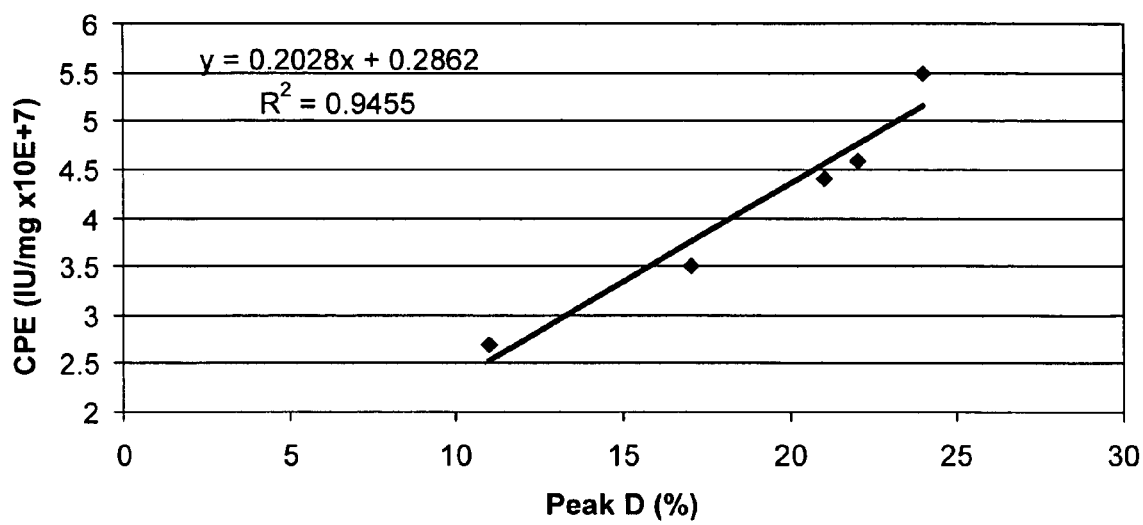
Figure 11:
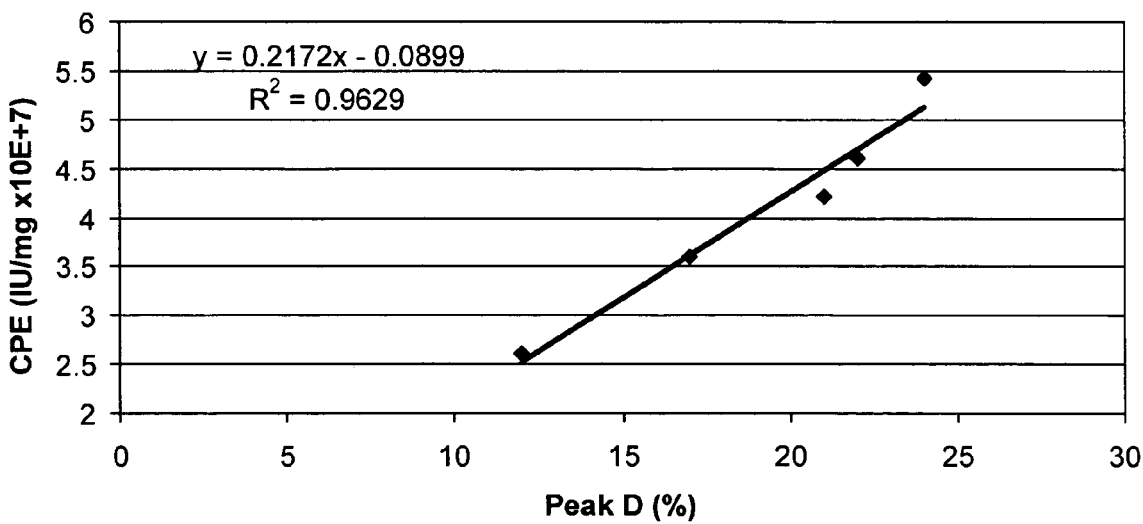

In the synthetic protein analog of the invention, the cysteine 17 residue may be replaced by a serine, threonine, glycine, alanine, valine, leucine, isoleucine, histidine, tyrosine, phenylalanine, tryptophan or methionine. In a specific embodiment, the substitution is serine 17. The asparagine 25 residue has been replaced by an aspartate, iso-aspartate or a cyclic imide. Referring to FIG. 2, the primary (amino acid sequence (SEQ ID NO: 2)) and secondary (folding, cross-linking) structure of a IFN-β 1b protein analog in accordance with the invention is illustrated. At position 25, the native Asn residue is deamidated. The deamidation of the asparagine occurs via a cyclic imide intermediate. This pathway is illustrated in FIG. 3. As described in further detail below, Glu-C peptide map results indicate that the major forms of deamidation are iso-Asp (IFN-$\beta_{ser17,iso-asp25}$) and cyclic imide (IFN-$\beta_{ser17,cyclic-imide25}$).

The protein analog may be made by a combination of recombinant synthetic and chemical modification techniques. Initially, the IFN-β 1b synthetic protein analog is typically made by recombinant DNA directed mutagenesis techniques, as described in the patents referenced above in the Background section of the application. Directed mutagenesis techniques are well known and have been reviewed by Lather, R. F. and Lecoq, J. P. in Genetic Engineering Academic Press (1983) pp 31-50. Oligonucleotide-directed mutagenesis is specifically reviewed by Smith, M. and Gillam, S. in Genetic Engineering: Principles and Methods, Plenum Press (1981) 3:1-32.

The IFN-β 1b protein analog is then subjected to a chemical treatment that deamidates the asparagine residue at position 25. There are a number of possible deamidation techniques that may be effective and suitable for adoption in large scale pharmaceutical manufacturing and any technique that accomplishes the deamidation while retaining a native biological activity, preferably an increased biological activity, may be used. Broadly speaking, deamidation of IFN-β proteins can be achieved by incubation at moderate to high temperature (e.g., about 25-60° C.) and a variety of pHs, from low (e.g., about 0-4) moderate (e.g., about 4-10) to high (e.g., about 10-14) with reaction times from about 1 minute to about 90 days or more, depending upon conditions. For example, deamidation may be accomplished by incubation of IFN-β (e.g., IFN-β 1a or INF-β 1b) for up to 60° C.; or between about 25 and 40° C., for example about 40° C., at about pH 4 for at least 24 hours, for example up to 40 days. The reaction time may be decreased and/or the reaction temperature decreased by raising the pH, for example to a neutral to basic pH of about 7 up to 14, for example for about 8 to 12, e.g., about 8.5. In one example, the biological activity (CPE) of a sample of INF-β 1b increases almost 2-fold after treatment at pH 8.4 at 2-8° C. for 14 days to about 4.5 IU/mg. Substantial activity increases have also been observed for treatments at moderate (e.g., room temperature) to high (e.g., 37-40° C.) temperature for 14-40 days.

The techniques for preparing the deamidated IFN-β protein analog may produce a product that is partially or substantially pure. For example, at least 25%, at least 50%, at least 75% or substantially all of the synthetic protein analog in the product may be deamidated at position 25, numbered in accordance with native interferon-β. Where less than substantially all of the product is deamidated, the product may nevertheless show increased biological activity and HA-free stability. In some instances, it may be desirable to purify and isolate the deamidated protein analog(s) in the product. This purification and isolation may be achieved by cationic exchange HPLC for example using the following conditions:

Chromatography Stationary Phase: Pharmacia Mono S HR 5/5, or equivalent;

Eluent Buffer: 20 mM Tris-HCl, pH 7.0 with 0.5% Empigen;

Gradient: NaCl linear gradient up to 200 mM or higher in the eluent buffer.

For manufacturing, this technique can be conducted on a large scale.

In a preferred embodiment, when the synthetic protein analog is microbially produced, it is unglycosylated. Also, the protein analog has an N-terminal methionine deletion. In other embodiments, the protein analog may be produced in mammalian cells and thus be glycosylated.

As described in further detail below, various activity assays demonstrate that deamidated IFN-β 1b protein analogs have increased bioactivity relative to their parent IFN-β proteins. And the stability results have been obtained with HA-free samples indicating that the deamidated IFN-β protein analogs of the present invention are suitable for HA-free formulation as a therapeutic. To form a therapeutic composition, the protein analog, partially or substantially pure as described above, can be admixed with a pharmaceutically acceptable carrier medium, such as are well known for this type of therapeutic product.

While it is an advantageous property of compositions of the present invention that they exhibit HA-free stability, the deamidation may also be conducted for HA-containing formulations and these are not excluded from the scope of the present invention. In addition, while the invention is primarily described here with reference to IFN-β 1b protein analogs, the invention is also applicable to other IFN-β analogs, including IFN-β 1a analogs.

The IFN-β protein analogs and compositions of the present invention exhibit biological activity that suggest utility in therapeutics in a number of applications including regulating cell growth in a patient, treating a patient for viral disease and stimulating natural killer cell activity in a patient. One particular use is for treating multiple sclerosis in a patient, in particular relapsing-remitting MS. In this respect, therapeutics in accordance with the present invention are useful in treatment for reducing the frequency of multiple sclerosis flare-ups. The increased level of biological activity of the deamidated IFN-β protein analogs indicates enhanced effects as therapeutics, for example in the treatment and management of MS.

According to another aspect of the present invention, an endoproteinase-C (Glu-C) peptide map technique is provided. The peptide map produces a fingerprint profile for proteins using an enzymatic digest of a reduced protein sample at a relatively low pH, followed by liquid chromatographic (e.g., RP-HPLC) resolution of the digest fragments. The peptide mapping may be used in quality control as an ID test for deamidated IFN-β protein analog product in accordance with the invention. It is also a powerful tool to monitor minor primary structure modifications in a protein from events such as clipping, mutation and degradation due to oxidation or deamidation.

One variant of deamidated IFN-β is known to contain cyclic imide, an intermediate form of deamidation. This cyclic imide from is found in increased amounts in stability samples. Most enzymes including Lys-C, which is used in a conventional peptide map for IFN-β, optimally digest proteins at neutral to high pH. At neutral to high pH, the cyclic imide is unstable and further deamidation is artificially induced. Therefore, maintaining the sample at a low pH environment during reduction and digestion is necessary to monitor the native level of both cyclic imide and other deamidation froms (Asp, iso-Asp) in the sample.

The endoproteinase-C (Glu-C) peptide map is coupled with a reducing agent that is functional at a pH of below 8, e.g., in the range of about 3-8, for example about 3, 4, 5, 6, 7 or 8 or pHs intermediate those. A suitable reducing agent is tris-(2-carboxyethyl) phosphine (TCEP). Other reducing agents functional at a pH of about 3-8 may be used, such as dithiothreitol (DTT), 2-mercaptoethanol, cysteine, reduced glutathione, 2-mercaptoethylamine and thioglycollic acid. The Glu-C peptide map has two optimal pHs, pH 7.8 and pH 4.0, for its enzymatic activity. As noted above, TCEP is known to be functional at pH below 8.0. In one embodiment, the new Glu-C peptide map uses the sample preparation including both reduction by TCEP and digestion at low pH, 4.0, which is at the optimal pH range to preserve the native level of deamidated forms, e.g., cyclic imide, in the sample. This new map technique may be used to characterize the digest fragment containing deamidated forms, including cyclic imide, in IFN-β samples.

IFN-β samples may be tested by the Glu-C peptide map to identify the deamidation site and its form (e.g., Asp, Iso-Asp, cyclic imide). Protein samples in buffered formulations (e.g., 0.5 ml protein sample at a concentration of 0.1 to 10, e.g., 0.5 mg/ml in formulation buffer of 2 to 500 mM buffer, or in some cases 50 to 100 mM, of a salt such as aspartate, bicarbonate (e.g., ammonium bicarbonate), carbonate (e.g., ammonium carbonate), acetate (e.g., ammonium acetate), phosphate (e.g., sodium phosphate), citrate, formate, succinate, MES, PIPES, ACES, MOPS, MOPSO, HEPES, TES, TRIS-HCl, BIS-TRIS, BIS-TRIS Propane, ADA, BES, DIPSO, TAPSO, HEPPSO, POPSO, EPPS, TEA, etc. the appropriate selection and use of which will be known to those of skill in the art for the desired pH (e.g., 2 mM aspartic acid, pH 4)) can be reduced using TCEP, for example using a 1:2 to 1:30, e.g., 1:3, 1:4, 1:5, 1:10 or 1:20 molar ratio of protein to TCEP, such as 1:10. The sample is incubated, for example at about 30-40° C. (e.g., 37° C.), until the sample material is reduced. Suitable incubation times may be from about 5 minutes to 24 hours depending on sample lability, for example 3 hours. The reduced material is subsequently digested with Glu-C, for example 1 to 10, e.g., 4 mg/ml, at a 1:1 to 20:1 (or any suitable intermediate ratio including 2:1, 3:1, 4:1, 10:1, etc.), e.g., 5:1, mass ratio of protein to Glu-C and incubated, for example at about 30-40° C. (e.g., 37° C.), until the sample material is digested. Suitable digestion times may be from about 5 minutes to 24 hours depending on sample lability, for example 4 hours. The peptide fragments can be resolved by liquid, e.g., RP-HPLC, chromatography.

A specific peptide map experiment and its results are described in the Examples section below.

EXAMPLES

The following examples illustrate aspects of the present invention, but are not intended in any way to limit the invention. In various of these examples, a distinction is made between the cyclic imide and other deamidated forms (Asp and iso-Asp), the two main distinguishable species that showed increase of potency. All are deamidated forms, but where a distinction is drawn between the cyclic imide and the other deamidated forms (Asp and iso-Asp) the former is sometimes referred to as "cyclic imide" while the latter is sometimes referred to as "deamidated" or "deamidation," particularly in the figure labels.

Example 1

Potency Increase in HA-Free IFN-β 1b Stability Sample

SUMMARY

A potency increase has been observed in HA-Free IFN-β 1b stability samples. The cytopathic effects (CPE) bioassay showed a potency increase in HA-Free IFN-β 25° C. stability samples in the course of time (T=0-6 months). The final deamidation product and its intermediate, cyclic imide, have also been observed to be increased in 25° C. stability samples.

Glu-C peptide mapping identified the deamidation site at Asn25 and revealed that the major forms of deamidation in the HA-free IFN-β 1b stability samples were the iso-Asp and cyclic imide analogs, while the Asp form is slightly increased.

The results obtained from RP-HPLC method indicated that the deamidated forms (cyclic imide, Asp and iso-Asp) significantly increased in HA-free IFN-β stability sample.

The deamidated forms in the HA-free IFN-β stability sample showed higher biological activity than the parent (amidated) IFN-β by CPE and antiproliferative assays.

Based on these findings, the deamidation (forming Asp, iso-Asp and cyclic imide analogs) is considered to enhance a biological activity of HA-free IFN-β. Therefore, a deamidated form of IFN-β can be prepared in order to enhance a biological activity of IFN-β-based therapeutics, either HA-free or HA-containing. The deamidated analogs can be prepared by incubating an IFN-β solution (either HA-free or HA-containing) at moderate to high temperature, and/or at low, moderate or high pH. The deamidated products of this invention will reduce the required clinical dose and increase the stability of liquid IFN-β formulations at room temperature. By lowering the clinical dose, the proportion of patients experiencing an adverse immune reaction (e.g., neutralizing antibodies), is reduced.

Data substantiating the invention obtained from various, stability studies and analyses of IFN-β 1b preparations are provided below:

1. HA-Free IFN-β Stability Data

As shown below in Table 1 (Drug Substance: in 2 mM Aspartic acid, pH 4.0) and Table 2 (Drug Product: in 2 mM Aspartic acid, pH 4.0, 9% Trehalose), the cytopathic effects (CPE) bioassay showed a potency increase in HA-free IFN-β 1b 25° C. stability samples in the course of time (T=0-6 months):

TABLE 1

CPE Bioassay Stability Data for the HA-Free Interferon beta 1b Drug Substance
Analytical Method: CPE Bioassay
Acceptance Criteria: 1.3 – 5.1 × $10^7$ IU/mg

| Lot No.: | Test Run | TA2040 | TA2085 | Test Run | TA2040 | TA2085 |
|---|---|---|---|---|---|---|
| Description: | 6 ml; 2 mg/ml | 6 ml; 2 mg/ml | 6 ml; 2 mg/ml | 6 ml; 2 mg/ml | 6 ml; 2 mg/ml | 6 ml; 2 mg/ml |
| Study No.: | 1402 | 1411 | 1414 | 1403 | 1412 | 1415 |
| Storage: | 5° C. | 5° C. | 5° C. | 25° C./60% RH | 25° C./60% RH | 25° C./60% RH |
| Orientation: | Upright | Upright | Upright | Upright | Upright | Upright |
| Months | IU/mg × $10^7$ | IU/mg × $10^7$ | IU/mg × $10^7$ | IU/mg × $10^7$ | IU/mg × $10^7$ | IU/mg × $10^7$ |
| 0 | 2.8 | 2.8 | 2.9 | 2.8 | 2.8 | 2.9 |
| 1.5 | ND | ND | ND | 4.2 | 3.5 | 3.6 |
| 3 | 3.0 | 2.9 | 2.8 | 4.6 | 4.2 | 4.1 |
| 4.5 | ND | ND | ND | 5.7 | 4.9 | 5.0 |
| 6 | 3.3 | 3.1 | 2.9 | 6.3 | 5.4 | 4.8 |

ND: Not Done RH: Relative Humidity

TABLE 2

CPE Bioassay Stability Data for the HA-Free Interferon beta 1b Drug Product

| Lot No.: | 14159-49 (Non-Clinical) | 25FEB03 (Test Run) | TA2158 | TA2451 |
|---|---|---|---|---|
| Description: | 1.2 ml; 0.25 mg/ml | 1.2 ml, 1.0 mg/ml | 1.2 ml, 1.0 mg/ml | 1.2 ml, 1.0 mg/ml |
| Study No.: | 1335 | 1438 | 1442 | 1444 |
| Storage: | 25° C./60% RH | 25° C./60% RH | 25° C./60% RH | 25° C./60% RH |
| Orientation: | Inverted | Inverted | Inverted | Inverted |
| Months | IU/mg × $10^7$ | IU/mg × $10^7$ | IU/mg × $10^7$ | IU/mg × $10^7$ |
| 0 | 2.8 | 2.7 | 2.7 | 2.6 |
| 1.5 | 3.2 | 3.7 | 3.5 | 3.6 |
| 3 | 4.3 | 4.4 | 4.4 | 4.2 |
| 4.5 | 4.1 | 4.8 | 4.6 | 4.6 |
| 6 | 4.6 | 5.3 | 5.5 | 5.4 |

As shown is Tables 3 and 4, below, cation exchange (CEX)-HPLC demonstrates that the stability data for 25° C. samples of drug substance and drug product, respectively, also showed an increase in deamidation (D-IFN-β):

Tables 5 and 6, below, show that an increase in Peak D, which represents the cyclic imide intermediate form of deamidation, was also observed in the course of time by using a

TABLE 3

CEX-HPLC Stability Data for the HA-Free Interferon beta 1b Drug Substance
Analytical Method: CEX HPLC
Acceptance Criterion: Report % Deamidation

| Lot No.: | Test Run | TA2040 | TA2085 | Test Run | TA2040 | TA2085 |
|---|---|---|---|---|---|---|
| Description: | 6 ml; 2 mg/ml | 6 ml; 2 mg/ml | 6 ml; 2 mg/ml | 6 ml; 2 mg/ml | 6 ml; 2 mg/ml | 6 ml; 2 mg/ml |
| Study No.: | 1402 | 1411 | 1414 | 1403 | 1412 | 1415 |
| Storage: | 5° C. | 5° C. | 5° C. | 25° C./60% RH | 25° C./60% RH | 25° C./60% RH |
| Orientation: | Upright | Upright | Upright | Upright | Upright | Upright |
| Months | % Deamidation | % Deamidation | % Deamidation | % Deamidation | % Deamidation | % Deamidation |
| 0 | 6 | 6 | 6 | 6 | 6 | 6 |
| 1.5 | ND | ND | ND | 10 | 10 | 9 |
| 3 | 7 | 6 | 7 | 14 | 14 | 13 |
| 4.5 | ND | ND | ND | 20 | 20 | 18 |
| 6 | 5 | 6 | 6 | 22 | 22 | 20 |

ND: Not Done

TABLE 4

CEX-HPLC Stability Data for the HA-Free Interferon beta 1b Drug Product

| Lot No.: | 14159-49 (Non-Clinical) | 25FEB03 (Test Run) | TA2158 | TA2451 |
|---|---|---|---|---|
| Description: | 1.2 ml; 0.25 mg/ml | 1.2 ml, 1.0 mg/ml | 1.2 ml, 1.0 mg/ml | 1.2 ml, 1.0 mg/ml |
| Study No.: | 1335 | 1438 | 1442 | 1444 |
| Storage: | 25° C./60% RH | 25° C./60% RH | 25° C./60% RH | 25° C./60% RH |
| Orientation: | Inverted | Inverted | Inverted | Inverted |
| Months | % Deamidation | % Deamidation | % Deamidation | % Deamidation |
| 0 | 4 | 7 | 7 | 7 |
| 1.5 | 7 | 11 | 13 | 12 |
| 3 | 12 | 18 | 18 | 17 |
| 4.5 | 16 | 24 | 24 | 22 |
| 6 | 18 | 37[1] | 35[1] | 40[1] |
| 10 | END | IP | IP | IP |
| | | END | | | reversed-phase (RP)-HPLC technique in 25° C. samples of drug substance and drug product, respectively:

TABLE 5

RP-HPLC Stability Data for the HA-Free Interferon beta 1b Drug Substance
Analytical Method: RP HPLC
Acceptance Criterion: Report % Peak Areas

| Lot No.: | Test Run | | | | | TA2040 | | | | | TA2085 | | | |
|---|---|---|---|---|---|---|---|---|---|---|---|---|---|---|
| Description: | 6 ml; 2 mg/ml | | | | | 6 ml; 2 mg/ml | | | | | 6 ml; 2 mg/ml | | | |
| Study No.: | 1403 | | | | | 1412 | | | | | 1415 | | | |
| Storage: | 25° C./60% RH | | | | | 25° C./60% RH | | | | | 25° C./60% RH | | | |
| Orientation: | Upright | | | | | Upright | | | | | Upright | | | |

| Months | Pk A | Main (D + B) | Pk D | Pk B | Other | Pk A | Main (D + B) | Pk D | Pk B | Other | Pk A | Main (D + B) | Pk D | Pk B | Other |
|---|---|---|---|---|---|---|---|---|---|---|---|---|---|---|---|
| 0 | 2 | 96 | 12 | 85 | 2 | 2 | 96 | 11 | 85 | 2 | 2 | 96 | 11 | 86 | 2 |
| 1.5 | 2 | 95 | 17 | 78 | 3 | 2 | 96 | 17 | 79 | 2 | 2 | 96 | 16 | 80 | 3 |
| 3 | 1 | 93 | 20 | 73 | 6 | 1 | 92 | 19 | 73 | 7 | 1 | 92 | 19 | 73 | 7 |
| 4.5 | 2 | 91 | 24 | 67 | 7 | 2 | 90 | 24 | 66 | 8 | 1 | 91 | 23 | 68 | 8 |
| 6 | 2 | 93 | 26 | 67 | 5 | 1 | 93 | 25 | 68 | 5 | 1 | 94 | 25 | 68 | 5 |

TABLE 6

RP-HPLC Stability Data for the HA-Free Interferon beta 1b Drug Product
Analytical Method: RP HPLC
Acceptance Criterion: Report % Peak Areas

| Lot No.: | 25FEB03 (Test Run) | | | | | TA2158 | | | | | TA2451 | | | |
|---|---|---|---|---|---|---|---|---|---|---|---|---|---|---|
| Description: | 1.2 ml, 1.0 mg/ml | | | | | 1.2 ml, 1.0 mg/ml | | | | | 1.2 ml, 1.0 mg/ml | | | |
| Study No.: | 1438 | | | | | 1442 | | | | | 1444 | | | |
| Storage: | 25° C./60% RH | | | | | 25° C./60% RH | | | | | 25° C./60% RH | | | |
| Orientation: | Inverted | | | | | Inverted | | | | | Inverted | | | |

| Months | Pk A | Main (D + B) | Pk D | Pk B | Other | Pk A | Main (D + B) | Pk D | Pk B | Other | Pk A | Main (D + B) | Pk D | Pk B | Other |
|---|---|---|---|---|---|---|---|---|---|---|---|---|---|---|---|
| 0 | 1 | 93 | 12 | 81 | 6 | 1 | 93 | 11 | 82 | 6 | 1 | 93 | 12 | 81 | 6 |
| 1.5 | 1 | 92 | 16 | 76 | 6 | 1 | 92 | 17 | 74 | 7 | 1 | 91 | 17 | 75 | 8 |
| 3 | 2 | 90 | 22 | 68 | 8 | 2 | 91 | 21 | 69 | 8 | 2 | 91 | 21 | 70 | 7 |
| 4.5 | 2 | 94 | 23 | 71 | 5 | 1 | 94 | 22 | 72 | 5 | 1 | 94 | 22 | 72 | 4 |
| 6 | 1 | 94 | 24 | 70 | 5 | 1 | 94 | 24 | 71 | 5 | 1 | 95 | 24 | 71 | 4 |
| | | | | | | | END | | | | | | | | |

FIGS. 4-11 show plots of the potency versus the amount of deamidated IFN-β 1b ("% D-IFN" or "% Peak D") in various HA-free IFN-β stability drug substance and product lots in accordance with one aspect of the invention. These data demonstrate that there is a correlation between the potency increase and the level of deamidation of HA-free IFN-β.

2. Characterization of HA-Free IFN-β Stability Samples

The primary sequence of IFN-β 1b is shown in FIG. 3. Deamidation has been found to occur at Asn25. The nature of that deamidation and the properties of the deamidated products were explored in the assays described below:

2.1. Glu-C Peptide Map

A peptide map produces a fingerprint profile for proteins using an enzymatic digest followed by RP-HPLC. Peptide mapping is commonly utilized in quality control as an ID test. It is also a powerful tool to monitor minor primary structure modifications in a protein from events such as clipping, mutation and degradation due to oxidation or deamidation. HA-free IFN-β is known to contain cyclic imide, an intermediate form of deamidation. This cyclic imide is a key degraded variant in HA-free IFN-β and is found in increased amounts in stability samples. Most enzymes including Lys-C, which is used in the current peptide map for HA-free IFN-β, optimally digest proteins at neutral to high pH. At neutral to high pH, the cyclic imide is unstable and deamidation is artificially induced. Therefore, maintaining the sample at a low pH environment during reduction and digestion is necessary to monitor the native level of cyclic imide and deamidation in the sample.

A new endoproteinase-C (Glu-C) peptide map has been developed coupled with tris-(2-carboxyethyl) phosphine (TCEP) as reducing agent to characterize the fragment containing deamidated forms, including cyclic imide, in HA-free IFN-β. The Glu-C peptide map is known to have two optimal pHs, pH 7.8 and pH 4.0, for its enzymatic activity. The TCEP is known to be functional at pH below 8.0. The new Glu-C peptide map was developed using the sample preparation including both reduction and digestion at low pH, 4.0, which is at the optimal pH range to preserve the native level of deamidated forms, e.g., cyclic imide, in the sample. Since the peptide map developed here employs a low pH sample preparation, the accurate monitoring of the native level of deamidated forms in HA-free IFN-β is successfully achieved.

Stability samples of HA-Free IFN-β 1b drug product lot TA2451 (3, 6, and 9 months at 25° C.) were tested by Glu-C peptide map to identify the deamidation site and its form (e.g., Asp, Iso-Asp, cyclic imide). Each 0.5 ml protein sample at a concentration of 0.5 mg/ml in formulation buffer of 2 mM aspartic acid, pH 4.0 was reduced using TCEP. Using a 1:10 molar ratio of protein to TCEP, the sample was incubated at 37° C. for 3 hours. The reduced material was subsequently digested with 4 mg/ml Glu-C at a 5:1 mass ratio of protein to Glu-C and incubated at 37° C. for 4 hours. The peptide fragments were resolved by RP-HPLC chromatography (ThermoHypersil BioBasic C18, 150×4.6 mm, 5 µm), using an acetonitrile gradient in 0.1% trifluoroacetic acid as elution buffer, at a flow rate of 1.0 ml/min and a column temperature at 38° C.

Figure 12A:
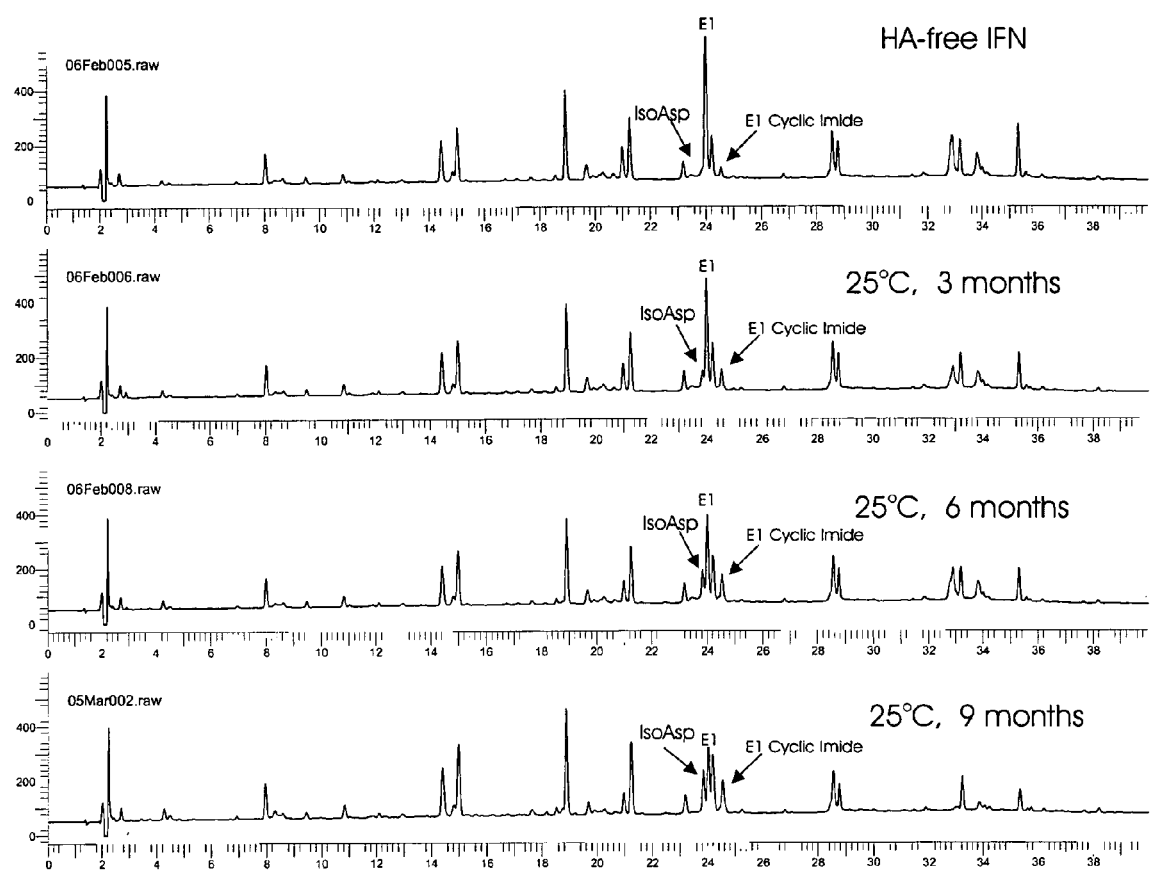
FIG. 12A shows Glu-C peptide maps of HA-Free IFN-β stability samples in accordance with one aspect of the invention.
Figure 12B:
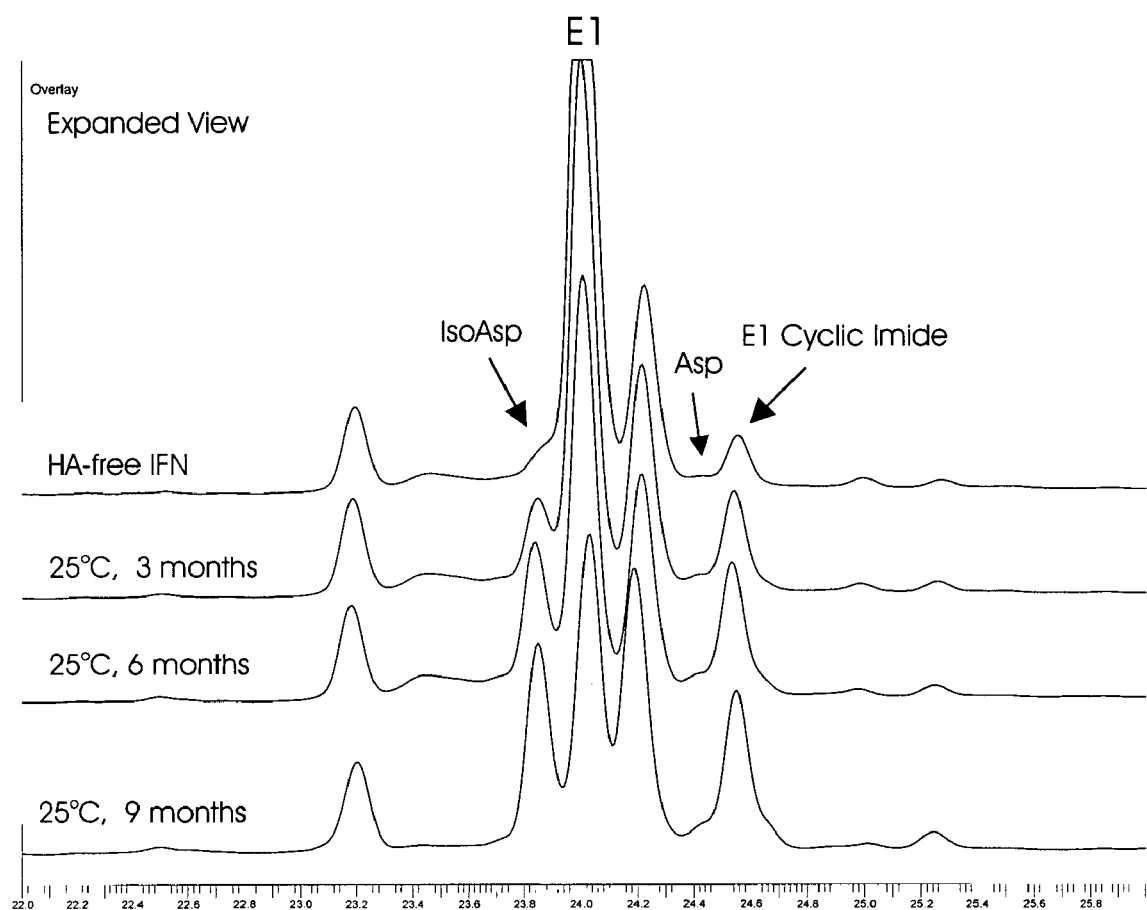
FIG. 12B shows an expanded view a portion of the map of FIG. 12A.

FIG. 12A shows Glu-C peptide maps of HA-Free IFN-β stability samples in accordance with one aspect of the invention. FIG. 12B shows an expanded view of the 22-26 minute RT portion of the map of FIG. 12A.

As shown in the figures, the peak of fragment E1 decreased in the course of time, while the peaks representing iso-Asp, cyclic imide, and Asp increased. Those peaks are deamidated forms of Asn at position 25 in the fragment E1. This peak characterization was performed by mass spectrometry and Edman sequencing of E1 sub-fragments obtained by Lysyl endopeptidase digestion of E1-related fragments. The Asn25 residue has an amino acid sequence followed by glycine. This Asn-Gly sequence is known to have a fast rate of deamidation.

Based on this Glu-C peptide map result, the major forms of deamidation in the HA-free IFN-β stability samples were identified to be iso-Asp and cyclic imide. There was also a slight increase in the level of the Asp form.

2.2. RP-HPLC

Figure 13:
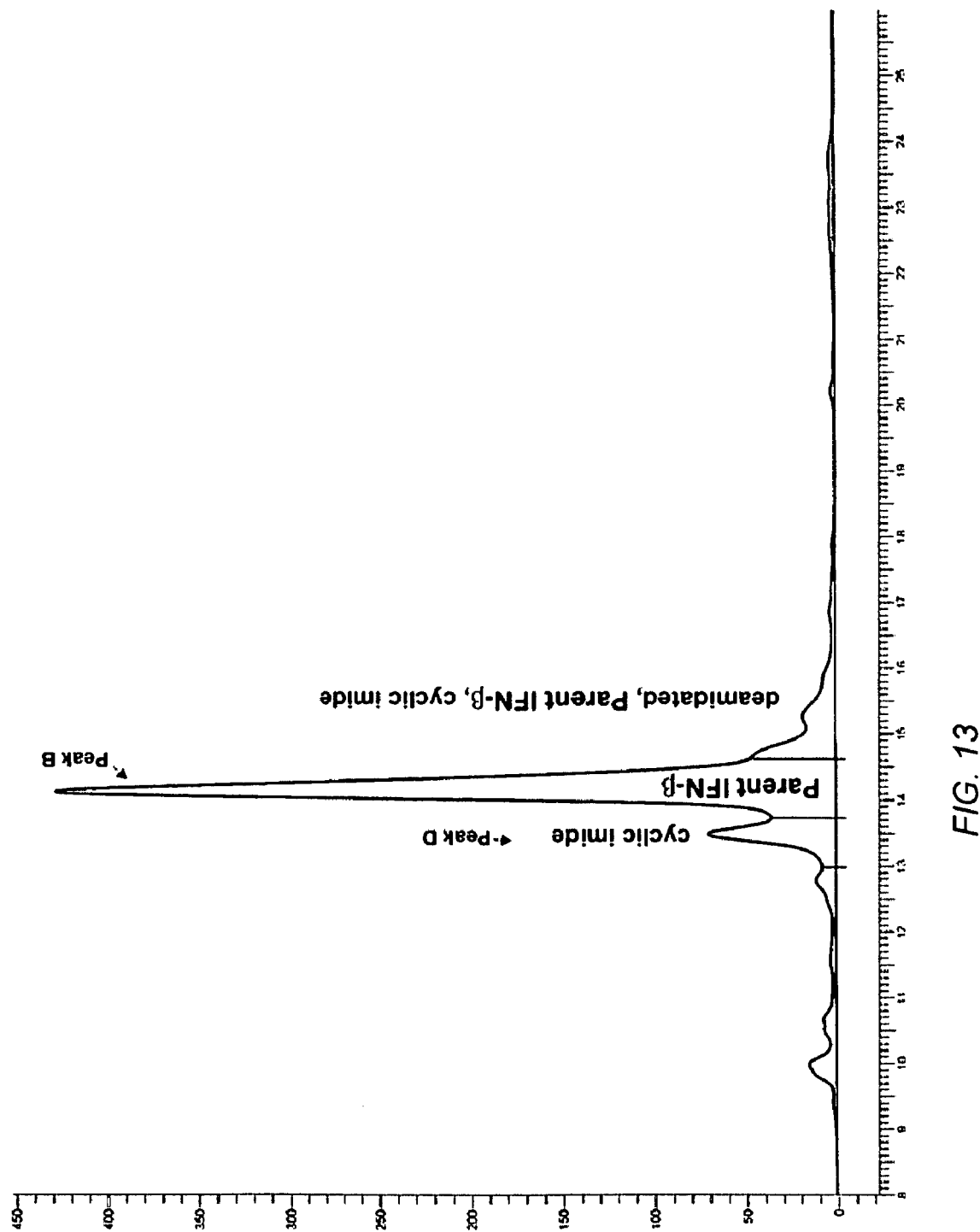
FIG. 13 shows the RP-HPLC profile of an HA-Free IFN-β control sample (time (min) vs. response (mV)).

RP-HPLC separates compounds based on their hydrophobicity. HA-free IFN-β 1b samples were tested by RP-HPLC method to characterize IFN-β 1b variants (e.g., Asp, iso-Asp, cyclic imide). The test samples were injected onto a Zorbax 300SB-CN, 150×4.6 mm, 3.5 µm particle size, chromatography column and IFN-β 1b variants were separated using an acetonitrile gradient in 0.1% trifluoroacetic acid elution buffer. The control sample result is shown in FIG. 13.

The peak identification shown in the figure was performed by the online LC/mass spectrometric analysis (RP-HPLC/Q-TOF/ESI-MS). The HPLC flow was split approximately 1:20, and about 50 ul/min was directed to the ion source of the mass spectrometer. The mass spectrometer was a Micromass Q-TOF2 instrument, with an electrospray ion source. The ion voltage was set at 3200, with the cone voltage set at 50. Data was collected with the time-of-flight (TOF) analyzer between m/z 300 and 2500. The online LC/mass data reveals that there is more than one protein variant co-eluting under some of the RP-HPLC peaks.

Figure 14:
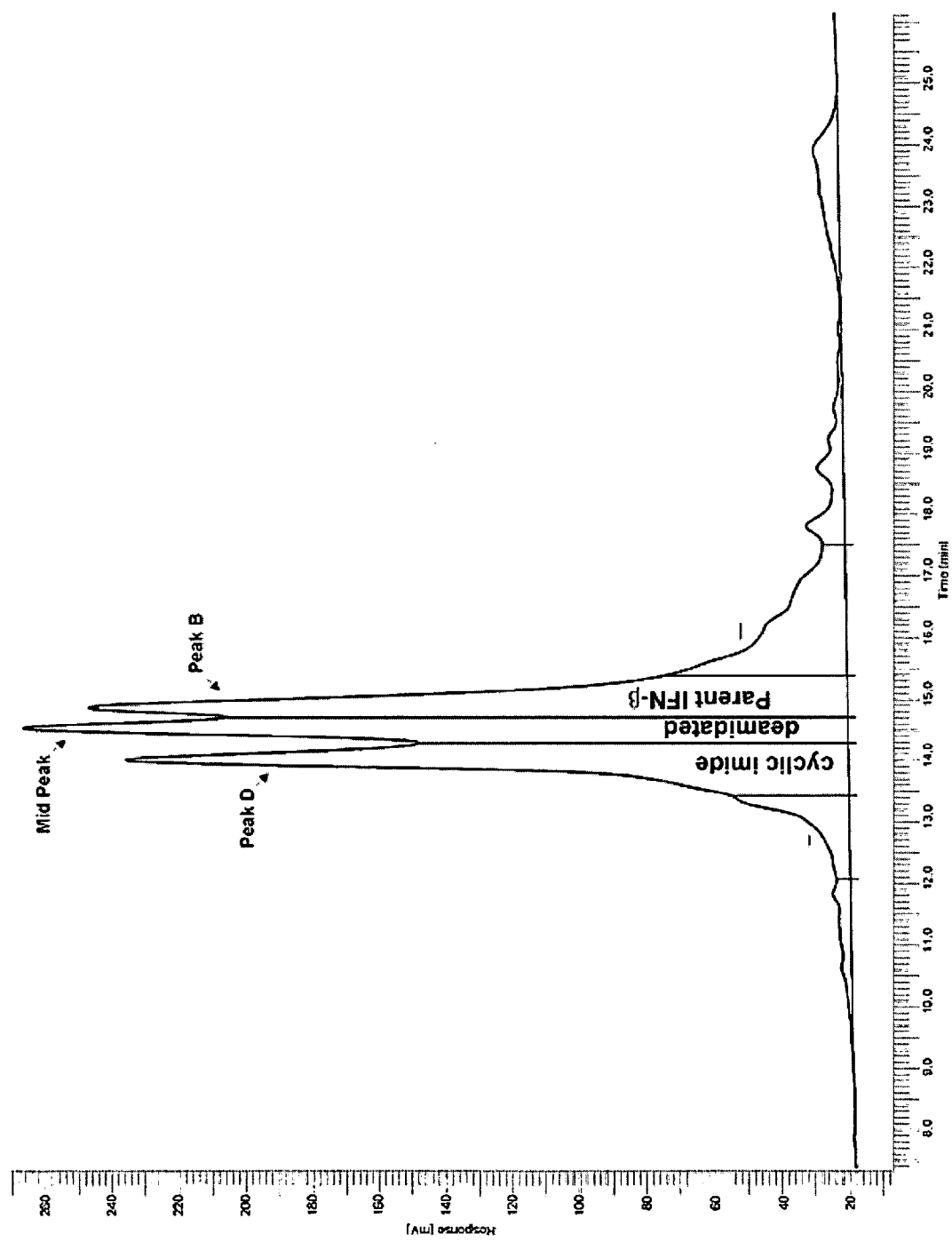
FIG. 14 shows the RP-HPLC profile of the stability sample of the HA-free IFN-β 1b drug product lot in accordance with one aspect of the invention.

FIG. 14 shows the RP-HPLC profile of the stability sample of the HA-free IFN-β 1b drug product lot (about 10 months at 25° C.). As shown in the figure, the profile is different from that of control sample (FIG. 13) and cyclic imide (Peak D) and deamidation (Asp and/or iso-Asp) (Mid Peak) significantly increased in HA-free IFN-β 1b. Multiple minor other deamidated and cyclic imide variants are observed. These are deamidated and cyclic imide variants with additional structural and chemical modifications that are separated due to their differing hydrophobic properties.

2.3. CPE Bioassay

IFN-β induces an antiviral state in mammalian cells in which some virus types are inhibited from replicating and causing cellular cytopathic effects (CPE). A549 human lung carcinoma cells and murine encephalomyocarditis (EMC) virus were used to evaluate biological activity of the RP-HPLC fractions obtained from the stability sample of the HA-free IFN-β 1b drug product lot (about 10 months at 25° C.).

Cells were grown in 96-well plates and treated with serial dilutions of IFN-β 1b overnight before addition of virus. Cultures were then incubated for a suitable period of time to allow virus replication. Cells treated with sufficient IFN-β 1b were protected from the virus challenge and remain viable. Unprotected cells underwent cytopathic changes and died. The interferon dose dependent CPE was quantitated using staining techniques and a dose response curve prepared from a plot of cell viability (Optical Density measurement) vs. IFN-β concentration. IFN-β activity was calculated as the concentration required for half maximal cell protection ($ED_{50}$ concentration).

Figure 15:
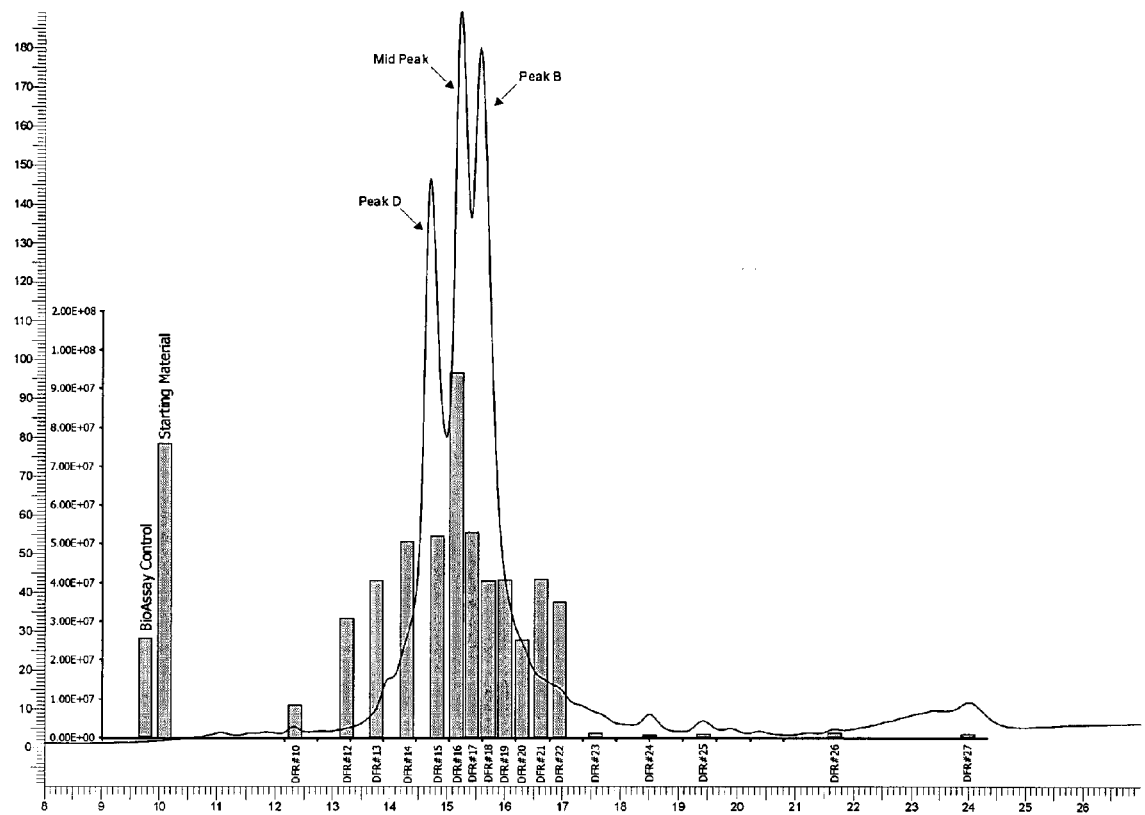
FIG. 15 shows a plot of the CPE Activity for RP-HPLC fractions of an HA-Free IFN-β stability sample in accordance with one aspect of the invention.

As shown in FIG. 15, the CPE activity in the deamidated fraction (Mid Peak, Fraction 16) is significantly higher than that in the parent IFN-β 1b fraction (Peak B, Fraction 18). The cyclic imide fraction (Peak D, Fraction 15) also shows higher CPE activity than the parent IFN-β 1b fraction.

2.4. Antiproliferative Assay

IFN-β shows antiproliferative activity against a number of cell lines established from human tumors. Two cell lines, Hs294T-a human melanoma cell line and Daudi-a human B lymphoblast line derived from Burkitt lymphoma, were used to evaluate biological activity of the RP-HPLC fractions obtained from the stability sample of the HA-free IFN-β 1b drug product lot (about 10 months at 25° C.).

Serial dilutions of the IFN-β test samples were performed in 96-well plates. Responder cells were prepared in tissue culture medium and added to the assay plates. After 3 days incubation, staining the cells with Alamar Blue or counting with a Coulter counter was used to measure the growth response. Cell growth was inhibited in response to IFN-β in a dose dependent manner. A dose response curve was prepared from a plot of cell number (Optical Density measurement) vs. IFN-β concentration. IFN-β activity was calculated as the concentration required for half maximal cell growth ($ED_{50}$ concentration).

Figure 16A:
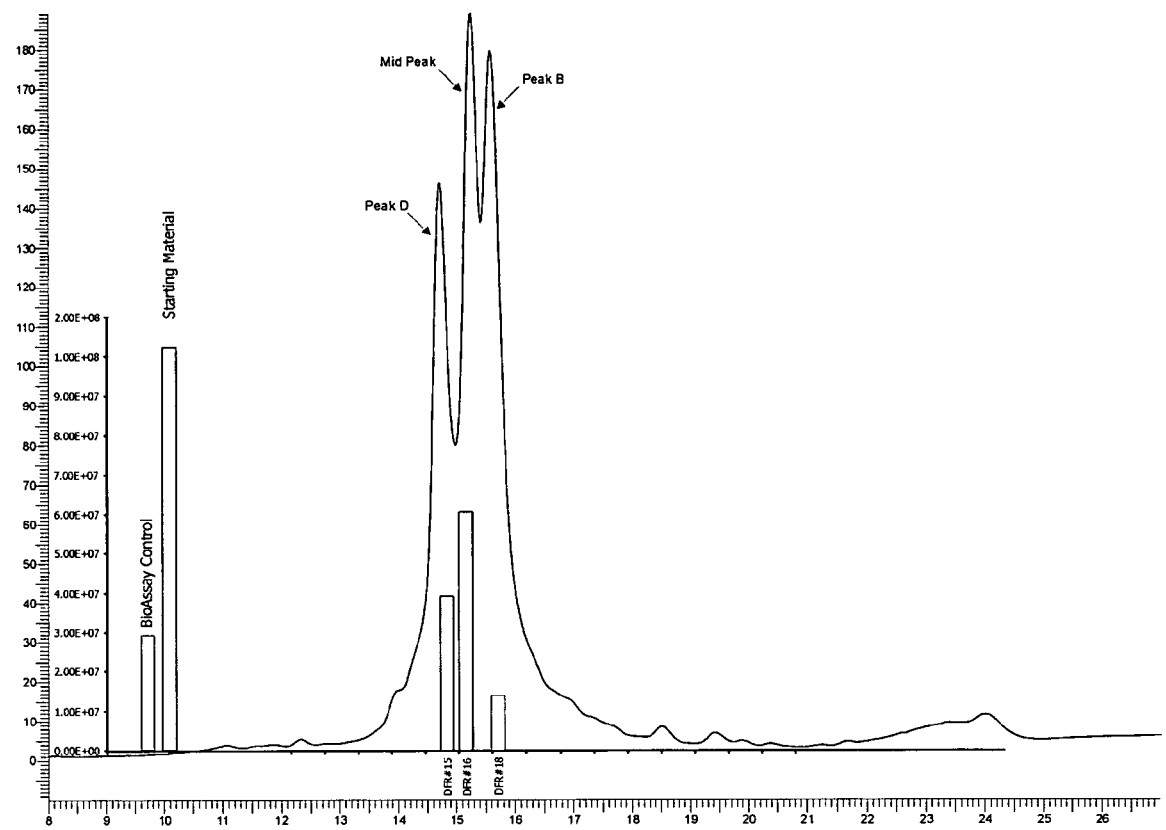
FIG. 16A shows a plot of results of an antiproliferative activity against Hs294T for RP-HPLC fractions of an HA-Free IFN-β stability sample in accordance with one aspect of the invention.
Figure 16B:
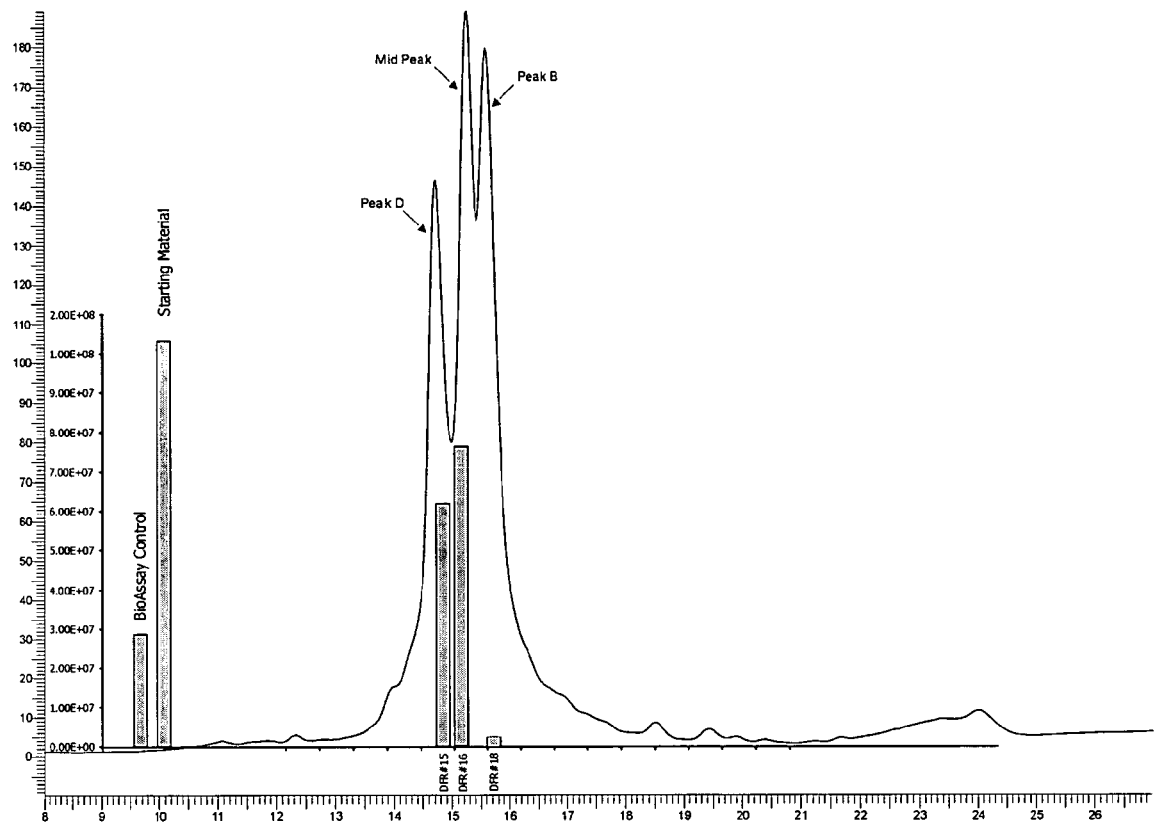
FIG. 16B shows a plot of results of an antiproliferative activity against Daudi for RP-HPLC fractions of an HA-Free IFN-β stability sample in accordance with one aspect of the invention.

As shown in FIGS. 16A (Hs294T) and 16B (Daudi), the antiproliferative activity in the deamidation fraction (Mid Peak, Fraction 16) and cyclic imide fraction (Peak D, Fraction 15) is significantly higher than that in the parent IFN-β fraction (Peak B, Fraction 18).

3. Conclusions

Based on the stability data and results obtained from studies described above, deamidation (Asp, iso-Asp and cyclic imide replacing Asn at position 25) enhances a biological activity of IFN-β. Therefore, a deamidated form of an IFN-β, e.g., IFN-β 1b can be intentionally prepared in order to enhance the compound's biological activity. The deamidated form can be prepared by incubating IFN-β at moderate to high temperature, or at low, moderate or high pH environment. The deamidated products of this invention will reduce the required clinical dose and increase the stability of liquid IFN-β formulations, including HA-free and HA-containing IFN-β formulations, at room temperature. By lowering the clinical dose, the proportion of patients experiencing an adverse immune reaction (e.g., neutralizing antibodies), is reduced.

Example 2

Manufacturability Data

Experiments were conducted to demonstrate various deamidation techniques, as described above. The data obtained from the CPE bioassay evidences that deamidated IFN-β is readily prepared by processes suitable for large scale pharmaceutical production. In particular, significant bioactivity increases were observed in various samples manufactured under Good Manufacturing Practices (GMP) incubated at moderate (e.g., room temperature) to high (e.g., 37-40° C.) temperature for 14-40 days, and bioactivity increases of almost 2 fold were obtained by incubating a GMP sample at room temperature and pH 8.8 for about 1 hour, and at 2-8° C. at pH 8.4 for about 14 days.

CPE Bioassay Results

| CPE Bioassay Results | |
|---|---|
| Sample Name | IU/mg |
| Test 1 | |
| TR090602 Bulk | 2.79E+07 |
| TR090602 Stab RT[1] 20 days | 3.87E+07 |
| TR090602 Stab 37C 20 days | 4.11E+07 |
| Stressed HA Free Control | 2.95E+07 |
| Stressed HA Free Base pH[2] | 4.52E+07 |
| Stressed HA Free 40C 30 Days | 5.06E+07 |
| IFN CPE Assay Control | 2.94E+07 |
| Test 2 | |
| TR090602 Bulk | 3.62E+07 |
| TR090602 Stab RT 40 days | 6.52E+07 |
| TR090602 Stab 37C 40 days | 1.56E+08 |
| GMP#1 Bulk | 2.67E+07 |
| GMP#1 Bulk Stab 37C 40 days | 3.51E+07 |

| CPE Bioassay Results -continued | |
|---|---|
| Sample Name | IU/mg |
| GMP#1 Bulk pH 8.8[3] | 4.79E+07 |
| Stressed HA free Control | 2.26E+07 |
| Stressed HA free 40C 14 days | 3.44E+07 |
| Stressed HA free 40C 30 days | 4.05E+07 |
| IFN CPE Assay Control | 2.93E+07 |

[1]Room temperature
[2]Sample was incubated in pH 8.4 at 2-8C for 14 days.
[3]Sample was incubated in pH 8.8 at RT for 1 hr.

CONCLUSION

Although the foregoing invention has been described in some detail for purposes of clarity of understanding, it will be apparent that certain changes and modifications may be practiced within the scope of the appended claims. It should be noted that there are many alternative ways of implementing both the processes and compositions of the present invention. Accordingly, the present embodiments are to be considered as illustrative and not restrictive, and the invention is not to be limited to the details given herein, but may be modified within the scope and equivalents of the appended claims.

All documents cited herein are hereby incorporated by reference herein in their entirety and for all purposes.

What is claimed is:

1. A purified and isolated synthetic human interferon-β protein analog, wherein,
said protein analog differs in amino acid sequence from native human interferon-β, wherein native human interferon-β consists of the amino acid sequence set forth in SEQ ID NO:1, and wherein said protein analog differs in amino acid sequence from SEQ ID NO:1 at position 25, and optionally, at one or more positions selected from the group consisting of 1 and 17, numbered in accordance with SEQ ID NO:1;
the asparagine at position 25 is deamidated, and,
said protein analog exhibits a biological activity of native human interferon-β, wherein the biological activity is selected from the group consisting of inhibition of a virally-induced cellular cytopathic effect and an antiproliferative effect.

2. The synthetic protein analog of claim 1, wherein the cysteine at position 17 is deleted or replaced by a neutral amino acid.

3. The synthetic protein analog of claim 2, wherein said cysteine residue has been replaced by a serine residue.

4. The synthetic protein analog of claim 3, wherein said asparagine residue has been replaced by a residue selected from the group consisting of aspartate, iso-aspartate and cyclic imide.

5. The synthetic protein analog of claim 4, wherein the protein analog is unglycosylated.

6. The synthetic protein analog of claim 5, wherein the protein analog has an N-terminal methionine deletion.

7. The synthetic protein analog of claim 4, wherein the protein analog has a biological activity greater than $IFN_{\beta ser17}$.

8. A therapeutic composition having IFN-β activity comprising a therapeutically effective amount of the synthetic protein analog of claims 4 admixed with a pharmaceutically acceptable carrier medium.

9. The composition of claim 8, wherein at least 50% of the synthetic protein analog is deamidated at position 25, numbered in accordance with native interferon-β.

10. The composition of claim 8, wherein substantially all of the synthetic protein analog is deamidated at position 25, numbered in accordance with native interferon-β.

11. The composition of claim 8, wherein the composition is HA-free.

* * * * *

UNITED STATES PATENT AND TRADEMARK OFFICE
CERTIFICATE OF CORRECTION

PATENT NO. : 7,595,040 B2 Page 1 of 1
APPLICATION NO. : 11/271516
DATED : September 29, 2009
INVENTOR(S) : Kenji Furuya et al.

It is certified that error appears in the above-identified patent and that said Letters Patent is hereby corrected as shown below:

Title Page, (*) Notice: Subject to any disclaimer, the term of this patent is extended or adjusted under 35 U.S.C. 154(b) by 252 days.

should read (*) Notice: Subject to any disclaimer, the term of this patent is extended or adjusted under 35 U.S.C. 154(b) by 509 days.

Signed and Sealed this

Twenty-seventh Day of April, 2010

David J. Kappos
*Director of the United States Patent and Trademark Office*

SEQUENCE LISTING

<160> NUMBER OF SEQ ID NOS: 2

<210> SEQ ID NO 1
<211> LENGTH: 166
<212> TYPE: PRT
<213> ORGANISM: Human

<400> SEQUENCE: 1

Met Ser Tyr Asn Leu Leu Gly Phe Leu Gln Arg Ser Ser Asn Phe Gln
1               5                   10                  15

Cys Gln Lys Leu Leu Trp Gln Leu Asn Gly Arg Leu Glu Tyr Cys Leu
            20                  25                  30

Lys Asp Arg Met Asn Phe Asp Ile Pro Glu Glu Ile Lys Gln Leu Gln
        35                  40                  45

Gln Phe Gln Lys Glu Asp Ala Ala Leu Thr Ile Tyr Glu Met Leu Gln
    50                  55                  60

Asn Ile Phe Ala Ile Phe Arg Gln Asp Ser Ser Ser Thr Gly Trp Asn
65                  70                  75                  80

Glu Thr Ile Val Glu Asn Leu Leu Ala Asn Val Tyr His Gln Ile Asn
                85                  90                  95

His Leu Lys Thr Val Leu Glu Glu Lys Leu Glu Lys Glu Asp Phe Thr
            100                 105                 110

Arg Gly Lys Leu Met Ser Ser Leu His Leu Lys Arg Tyr Tyr Gly Arg
        115                 120                 125

Ile Leu His Thr Leu Lys Ala Lys Glu Tyr Ser His Cys Ala Trp Thr
    130                 135                 140

Ile Val Arg Val Glu Ile Leu Ala Asn Phe Tyr Phe Ile Asn Arg Leu

-continued

```
145                 150                 155                 160
Thr Gly Tyr Leu Arg Asn
                165

<210> SEQ ID NO 2
<211> LENGTH: 165
<212> TYPE: PRT
<213> ORGANISM: Artificial Sequence
<220> FEATURE:
<223> OTHER INFORMATION: Human Interferon Beta 1b.

<400> SEQUENCE: 2

Ser Tyr Asn Leu Leu Gly Phe Leu Gln Arg Ser Ser Asn Phe Gln Ser
1               5                   10                  15

Gln Lys Leu Leu Trp Gln Leu Asn Gly Arg Leu Glu Tyr Cys Leu Lys
                20                  25                  30

Asp Arg Met Asn Phe Asp Ile Pro Glu Glu Ile Lys Gln Leu Gln Gln
            35                  40                  45

Phe Gln Lys Glu Asp Ala Ala Leu Thr Ile Tyr Glu Met Leu Gln Asn
    50                  55                  60

Ile Phe Ala Ile Phe Arg Gln Asp Ser Ser Ser Thr Gly Trp Asn Glu
65                  70                  75                  80

Thr Ile Val Glu Asn Leu Leu Ala Asn Val Tyr His Gln Ile Asn His
                85                  90                  95

Leu Lys Thr Val Leu Glu Glu Lys Leu Glu Lys Glu Asp Phe Thr Arg
                100                 105                 110

Gly Lys Leu Met Ser Ser Leu His Leu Lys Arg Tyr Tyr Gly Arg Ile
            115                 120                 125

Leu His Thr Leu Lys Ala Lys Glu Tyr Ser His Cys Ala Trp Thr Ile
    130                 135                 140

Val Arg Val Glu Ile Leu Ala Asn Phe Tyr Phe Ile Asn Arg Leu Thr
145                 150                 155                 160

Gly Tyr Leu Arg Asn
                165
```